United States Patent
Blust et al.

(10) Patent No.: US 10,330,677 B2
(45) Date of Patent: Jun. 25, 2019

(54) ELECTROCHEMICAL APTASENSORS WITH A GELATIN B MATRIX

(71) Applicant: Universiteit Antwerpen, Antwerp (BE)

(72) Inventors: Ronny J. P. Blust, Berchem (BE); Freddy Dardenne, Kontich (BE); Karolien De Wael, Sint-Pauwels (BE); Lucien Nagels, Heffen (BE); Guido F. E. Van Camp, Duffel (BE)

(73) Assignee: Universiteit Antwerpen, Antwerp (BE)

( * ) Notice: Subject to any disclaimer, the term of this patent is extended or adjusted under 35 U.S.C. 154(b) by 0 days.

(21) Appl. No.: 15/702,938

(22) Filed: Sep. 13, 2017

(65) Prior Publication Data
US 2018/0067108 A1    Mar. 8, 2018

Related U.S. Application Data

(62) Division of application No. 14/901,760, filed as application No. PCT/EP2014/064249 on Jul. 3, 2014, now Pat. No. 9,791,438.

(30) Foreign Application Priority Data

Jul. 4, 2013 (EP) .................................... 13175128

(51) Int. Cl.
*G01N 33/543* (2006.01)
*G01N 27/30* (2006.01)
*G01N 27/327* (2006.01)
*G01N 33/544* (2006.01)
*C12N 15/115* (2010.01)
*G01N 33/53* (2006.01)
*G01N 33/94* (2006.01)

(52) U.S. Cl.
CPC ..... *G01N 33/5438* (2013.01); *G01N 27/3275* (2013.01); *G01N 33/5308* (2013.01); *G01N 33/544* (2013.01); *G01N 33/5436* (2013.01); *G01N 33/946* (2013.01); *G01N 33/9413* (2013.01); *G01N 33/9446* (2013.01); *G01N 2333/78* (2013.01)

(58) Field of Classification Search
None
See application file for complete search history.

(56) References Cited

U.S. PATENT DOCUMENTS

| | | | |
|---|---|---|---|
| 7,857,962 B2 * | 12/2010 | Nagels | G01N 27/3335 204/417 |
| 9,791,438 B2 | 10/2017 | Blust et al. | |
| 2016/0377606 A1 | 12/2016 | Blust et al. | |

OTHER PUBLICATIONS

De Wael et al., "The electrochemistry of a gelatin modified gold electrode," Int J Electrochem Sci. 6:1810-9 (2011).
Pilehvar et al., "Aptasensing of chloramphenicol in the presence of its analogues: reaching the maximum residue limit," Anal Chem. 84:6753-8 (2012).

* cited by examiner

Primary Examiner — Tracy Vivlemore
(74) Attorney, Agent, or Firm — Clark & Elbing LLP

(57) ABSTRACT

This invention provides:—an aptamer-based electrochemical sensor, wherein said aptamer is covalently bonded to or chemisorbed on an electrode, said aptamer forming a complex with a target molecule and is encapsulated by a gelatin B matrix;—a method of manufacturing said aptamer-based electrochemical sensor;—the use of the aptamer-based electrochemical sensor for the electrochemical determination of a concentration of a target molecule; and—a composite electrode combining a polymeric material and electrically conducting particles for selective analyte detection, wherein said electrode is coated with gelatin type B.

11 Claims, 11 Drawing Sheets
Specification includes a Sequence Listing.

ELECTROCHEMICAL APTASENSORS WITH A GELATIN B MATRIX

CROSS-REFERENCE TO RELATED APPLICATIONS

This application is a divisional application of U.S. patent application Ser. No. 14/901,760 having a 371(c) date of Dec. 29, 2015, which is the U.S. National Stage of International Application No. PCT/EP2014/064249, filed on Jul. 3, 2014, which claims the benefit under 35 U.S.C. § 119(e) of European Patent Application No. 13175128.1, filed Jul. 4, 2013.

TECHNICAL FIELD OF THE INVENTION

The present invention relates to electrochemical aptasensors with a gelatin B matrix, a method of manufacturing the same and their use for determining target molecule concentrations. The present invention further relates to a composite electrode combining a polymeric material and electrically conducting particles for selective analyte detection.

BACKGROUND OF THE INVENTION

Electrochemical techniques are recognized as very important candidates for the development of biosensors to be used in non-specialized environments. Although there has been intensive research into amperometric biosensors and some of them have successfully reached the commercialization stage, there have been few reports of the use of biomolecules in potentiometric sensors except for the use of antibodies for the detection of bacteria, viruses and marker proteins via potentiometric principles.

De Wael et al. in Analytical Chemistry (2012) 84:4921-4927, reported the first use of potentiometric sensors to study molecular interactions in liquid environments with sensorgram methodology.

Aptamers have shown enormous potential in selectively detecting drugs, toxins, proteins etc. Sassolas et al., Electroanalysis 21(11) (2009) 1237-1250 reported the use of aptamers as the bio-recognition element in potentiometric sensors. When combined with Ion Sensitive Field Effect Transistors (ISFETS) as readout systems in poten-tiometric sensors, aptamers appear better than antibodies, due to their smaller size.

Pilehvar et al. in Anal. Chem. (2012) 84:6753-6758, reported a novel, label-free folding induced aptamer-based electrochemical biosensor for the detection of chloramphenicol (CAP) in the presence of its analogues.

Despite the fact that aptamers are chemically more stable than proteins, they have to be protected from nucleases. Moreover, in respect of electrochemical biosensors, the electrode surface also needs to be protected from unspecific adsorption and oxidation/reduction reactions occurring while analyzing real samples.

WO 2005/103664 discloses composite potentiometric electrodes for selective analyte detection in a sample comprising a sensing body made from a polymeric material, preferably plastified polyvinyl chloride, comprising:
  electrically conducting particles, preferably graphite powder, which increase in concentration away from a sample contact surface,
  ionophore molecules, which increase in concentration towards the sample contact surface, and
  an electrical connection, preferably made of copper, which passes proximal to said electrically conducting particles.

Selecting an appropriate host matrix for aptamers is one of the main challenges for the immobilization of aptamers in order to improve the analytical characteristics of aptasensors. There is also a need for more sensitive and more specific potentiometric sensors, in particular electrodes, to study molecular interactions in liquid environments with a sensorgram methodology.

SUMMARY OF THE INVENTION

It is an object of the present invention to provide more sensitive and more specific potentiometric sensors to determine the concentration of a variety of molecules such as vitamins, toxins, antibiotics, therapeutic drugs, diagnostic agents, recreational drugs, catecholamines, metabolites, proteins, cells etc. in liquid environments with sensorgram methodology and methods for using same.

Surprisingly it has been found that aptamers selected to form complexes, usually robust complexes, with target molecules such as vitamins, toxins, antibiotics, therapeutic drugs, diagnostic agents, recreational drugs, catecholamines, metabolites, proteins and cells, e.g. with dopamine and chloramphenicol, encapsulated in a hydrophilic gelatin B matrix can be used in electrochemical sensors to determine the concentrations of such target molecules in liquid environments using amperometric measurements or potentiometric measurements and exhibit higher sensitivity and selectivity to the target analyte than in the absence of the gelatin B matrix. Exemplary proteins include, but are not limited to, interferon γ. Exemplary therapeutic drugs include, but are not limited to, cell growth factors such as vascular endothelial growth factor, antigens (e.g. the prostate-specific antigen), promazine, lidocaine, ritodrine, bromhexine, clenbuterol, drofenine, atropine, salbutamol, trimipramine, fluphenazine, chlorpheniramine and catecholamines such as adrenaline, dopamine and noradrenaline. Exemplary toxins include, but are not limited to, cadaverine and dioxine, Exemplary recreational drugs include, but are not limited to, cocaine and functional equivalents thereof, and heroine.

Moreover, it has been surprisingly found that the use of type B gelatin encapsulation does not hinder the use of aptamers in such amperometric and potentiometric sensors, but also significantly increases the sensitivity of such sensors, whereas type A gelatin does not exhibit these advantageous properties. This cannot be explained by the difference in alkaline earth and alkali ion concentrations, since spiking of gelatin A with comparable alkaline earth and alkali ion concentrations had no effect on its behaviour. Without wishing to be bound by theory, this difference might be explainable by the difference in overall charge on the gelatin, since the negatively charged aptamer ions, being repelled by the overall negative charge of the gelatin B, would be more mobile and hence diffuse more rapidly to the electrode in a gelatin B matrix than in a gelatin A matrix in which the overall positive charge of the gelatin would result in attraction, and hence reduced diffusion, of the negatively charged aptamer molecules. This increased diffusion also reduces the effect of impurities in the gelatin.

Just as an example, in the case of an amperometric CAP-aptasensor with an aptamer linked to a gold surface by Au—S bonding, for example, see FIG. 1, in the absence of CAP thiolated aptamers encapsulated in gelatin B are partially un-folded and upon CAP introduction the aptamer switches its structure to bind CAP surprisingly bringing the redox active molecules proximate to the gold surface as characterised by their electrochemical behavior towards the target molecule CAP, scanning electron microscopy (SEM), cyclic voltammetry (CV) and electrochemical impedance spectroscopy (EIS) measurements, see FIG. 2.

A novel method of immobilizing aptamers on electrodes using, e.g. coated with, ionically conductive hydrophilic matrices, preferably negatively charged hydrophilic protein matrices like gelatin B, is provided. A preferred example of ionically conductive matrices is gelatin B providing a suitable micro-environment for aptamer immobilization, which facilitates the electron exchange between the target molecules and the electrode. The gelatin B film can be easily prepared and is stable over a long period. It has been found that Aptamers can be effectively immobilized on gold electrode surface by incorporation within the porous network of gelatin B. The three dimensional and hydrated environment of gelatin B helps to increase the sensitivity of the developed sensor by holding the aptamer onto the electrode surface and preventing the electrode surface from blocking. Sensors which are modified with gelatin B and aptamers show higher sensitivity toward CAP compared to the sensors without gelatin B as protective matrix. Moreover, the developed sensor is highly stable which makes it a promising technology for the fabrication of electrochemical aptasensors.

In a first aspect of the present invention, the above objective is realised by an aptamer-based electrochemical sensor, wherein said aptamer is covalently bonded to or chemisorbed on an electrode, said aptamer to form a complex, usually a robust complex with a target molecule and is encapsulated by a gelatin B matrix.

In a second aspect of the present invention, the above objective is realised by a method of manufacturing an aptamer-based electrochemical sensor for determining a concentration of a target molecule comprising the steps of: selecting an aptamer to form a complex, preferably a robust complex with a target molecule, e.g. using the SELEX procedure; synthesizing said aptamer; adsorbing said aptamer on or covalently coupling said aptamer with an electrode; and providing a gelatin B matrix for said aptamer on said electrode thereby realising said aptamer-based potentiometric sensor.

In a third aspect of the present invention, the above objective is realised by the use of the aptamer-based electrochemical sensor produced according to the second aspect of the present invention for the quantitative electrochemical determination of a concentration of said target molecule.

A specific embodiment of the present invention is the electrochemical determination of a concentration of chloramphenicol by an electrochemical sensor of the first aspect of the present invention, wherein said aptamer is AGC-AGC-ACA-GAG-GTC-AGA-TGA-CTG-AGG-GCA-CGG-ACA-GGA-GGG-CAT-GGA-GAG-ATG-GCG.

A specific embodiment of the present invention is the electrochemical determination of a concentration of chloramphenicol by an electrochemical sensor of the first aspect of the present invention, wherein said aptamer is AGC-AGC-ACA-GAG-GTC-AGA-TGA-CTG-AGG-GCA-CGG-ACA-GGA-GGG-GGA-GAG-ATG-GCG-TGA-GGT-CCT-ATG-CGT-GCT-ACC-GTG-AA.

Another specific embodiment of the present invention, the above objective is realised by the use for the electrochemical determination of a concentration of dopamine by an electrochemical sensor of the first aspect of the present invention, wherein said aptamer is GTC-TCT-GTG-TGC-GCC-AGA-GAA-CAC-TGG-GGC-AGA-TAT-GGG-CCA-GCA-CAG-AAT-GAG-GCC-C.

A fourth aspect of the present invention relates to a composite electrode combining a polymeric material and electrically conducting particles for selective analyte detection, wherein said electrode is coated with gelatin type B. Such gelatin-coated composite electrode may be a part of a three-electrode potentiometric cell for selective analyte detection, further comprising a reference electrode and a counter-electrode. This composite electrode and potentiometric cell may be for an in vivo analyte sensor or an in vitro analyte sensor.

Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention.

DEFINITIONS

The term "electrochemical biosensor", as used herein, means an analytical device that consist of a sensitive biological recognition material targeting an analyte of interest and a transduction element for converting the recognition process into an amperometric or potentiometric signal.

The term "sensorgram", as used herein, means a plot of the potentiometric signal vs. time, when a square concentration (block) pulse passes the sensor.

The term "sensorgram methodology", as used herein, means the use of the sensorgram to calculate $K_d$ values for the interaction between molecules, e.g. using the adsorption/desorption model described in K. De Wael et al., Anal. Chemistry 84 (2012) 4921-4927.

The term electrochemical aptasensor, as used herein, means an Electrochemical sensor with at least one immobilized aptamer as a sensing element.

The term aptamer, as used herein, means a synthetic oligonucleic acid sequence [single strand DNA or RNA] which can bind to a molecular target with high affinity and specificity, for instance due to its structural flexibility.

The term DNA-aptamer, as used herein disclosing the present invention, means a single strand synthetic DNA sequence which has been designed specifically to recognise and bind a particular molecular target such as a small molecule, a protein, a nucleic acid, a cell, tissue or an organism with high affinity and specificity, for instance due to their flexibility that results in binding to their ligands via adaptive recognition involving conformational alteration. DNA aptamers are advantageous over RNA aptamers due to the greater intrinsic chemical stability of DNA.

The term ionically conductive, as used in disclosing the present invention, means having an ionic conductivity greater than $10^{-5}$ S cm$^{-1}$, with ionic conductivities greater than $10^{-4}$ S cm$^{-1}$ being preferred and with ionic conductivities greater than $10^{-3}$ S cm$^{-1}$ being particularly preferred.

The term hydrophilic, as used herein, means having an affinity for attracting, adsorbing or absorbing water.

The term hydrogel, as used herein disclosing the present invention, is a colloid in which the disperse phase (colloid) has combined with the continuous phase (water) to produce a viscous jellylike product.

Gelatin, as used herein, refers to a product obtained by hot water extraction (hydrolysis) from the collagen protein from skin, bone and connective tissues of vertebrate animals (beef, pig, horse, fish). There are two main types of gelatin, referred to as A- (or acid) type and B- (or limed/alkaline) type. This categorization essentially goes back to the pretreatment of the raw material (collagen) which will affect the characteristics of the gelatin extracted. Gelatin gel strength is characterized by the Bloom number; the higher the Bloom number, the stronger the gel.

Gelatin normally slowly swells in cold water (18° C.) and more rapidly dissolves in aqueous solutions at 40° C. and above.

The term type B gelatin or gelatin B, as used herein, means a gelatin resulting from alkaline pretreatment of collagen. Type B gelatin typically has higher calcium, potassium and sodium ion concentrations than gelatin A, usually in the range of 900±100 ppm, 330±50 and 3600±1400 ppm respectively. Another typical difference of gelatin B is the iso-electric point (IEP) of 4.8 to 5.2 which is almost constant and independent of the Bloom number. This is in contrast with gelatin A, where the IEP is linked to the Bloom number and ranges from about 7 (low Bloom number i.e. 50-125) to about 9 (high Bloom number i.e. 225-325).

ABBREVIATIONS

The following abbreviations are used throughout the detailed description of the present invention with the following meanings.

CV: Cyclic Voltammetry.
SWV: Square Wave Voltammetry.
CAP: chloramphenicol.
DA: dopamine.
SELEX: "selection evolution of ligands by exponential enrichment".
MRL: Maximum residue limit.
FTIR: Fourier Transform Infrared Spectroscopy.
EIS: Electrochemical impedance spectroscopy.
SCE: Standard Calomel Electrode.
SPR: Surface Plasmon Resonance.
MES: 2-(N-morpholino)ethanesulfonic acid (a buffer).
IEP: isoelectric point.
FIA: flow injection analysis.
EDC: 1-ethyl-3(3-dimethylaminopropyl) carbodiimide.
NHS: N-hydroxysuccinimide.
SPE: screen printed electrode.

DESCRIPTION OF ILLUSTRATIVE EMBODIMENTS

The present invention will be described with respect to particular embodiments and with reference to certain drawings but the invention is not limited thereto but only by the claims.

It is to be understood that although preferred embodiments, specific constructions and configurations, as well as materials, are discussed herein for devices and methods according to the present invention, various changes or modifications in form and detail may be made, e.g. method steps or device components may be added, without departing from the scope and spirit of this invention.

versus tR (Transformed Response) curves (see equation (4) below) plotted against the DA concentrations which were used to record the sensorgrams.

Figure 13:
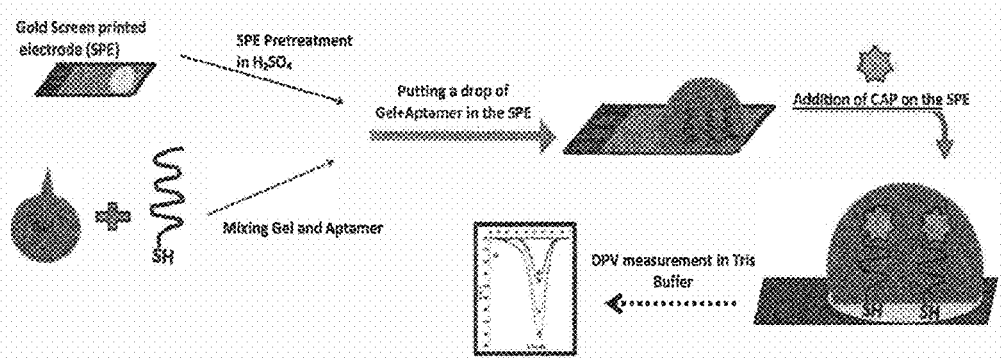

FIG. 13 shows the manufacture of a gelatin B-containing aptasensor based on a gold screen printed electrode (SPE) for the detection of CAP by means of differential pulse voltammetry.

Figure 14:
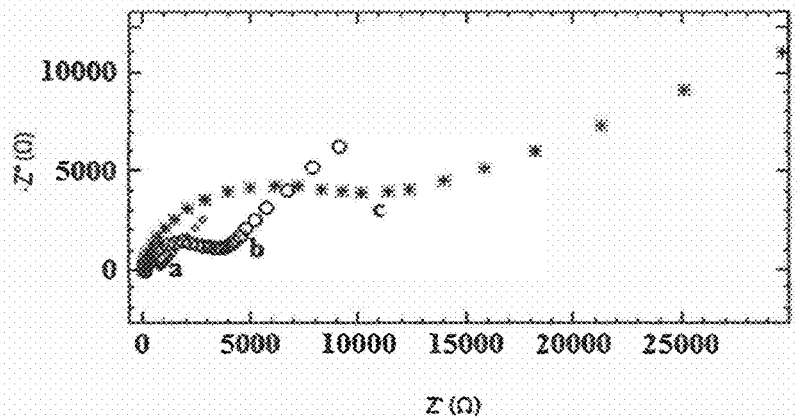

FIG. 14 shows electrochemical impedance spectra obtained with the bare SPE of FIG. 13 (FIG. 14a), the aptamer modified SPE (FIG. 14b) and the aptamer/gelatin B modified SPE (FIG. 14c).

Figure 15:
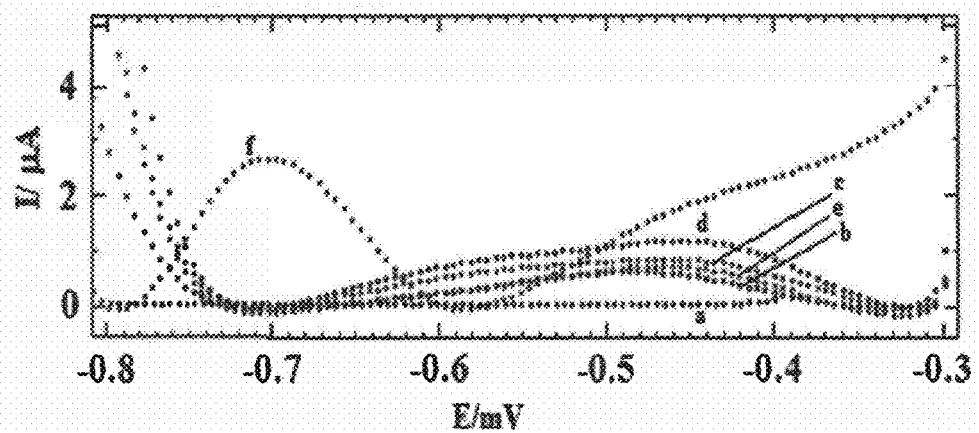

FIG. 15 shows the differential pulse voltammograms of accumulated CAP ($10^{-9}$ M) at the surface of the bare gold SPE of FIG. 13 (curve a), a gelatin A modified SPE (curve b), a gelatin B modified SPE (curve c), an aptamer modified SPE (curve d), an aptamer/gelatin A modified SPE (curve e) and an aptamer/gelatin B modified SPE (curve f) in tris buffer solution.

Figures 16A, 16B:
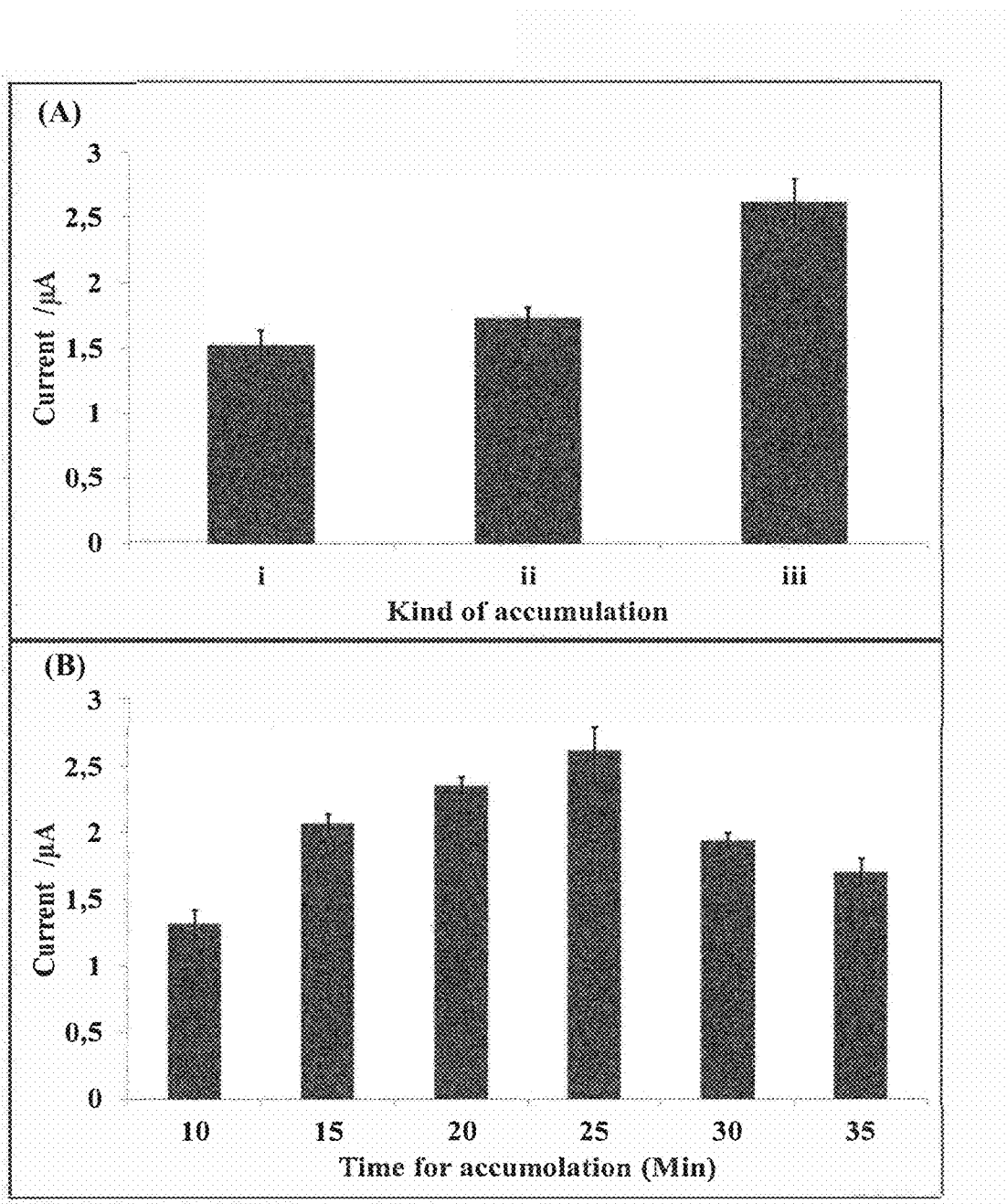

FIG. 16A and FIG. 16B show the influence of the kind (FIG. 16A) and time (FIG. 16B) of accumulation of CAP on the electrochemical detection signal.

Figures 17A, 17B:
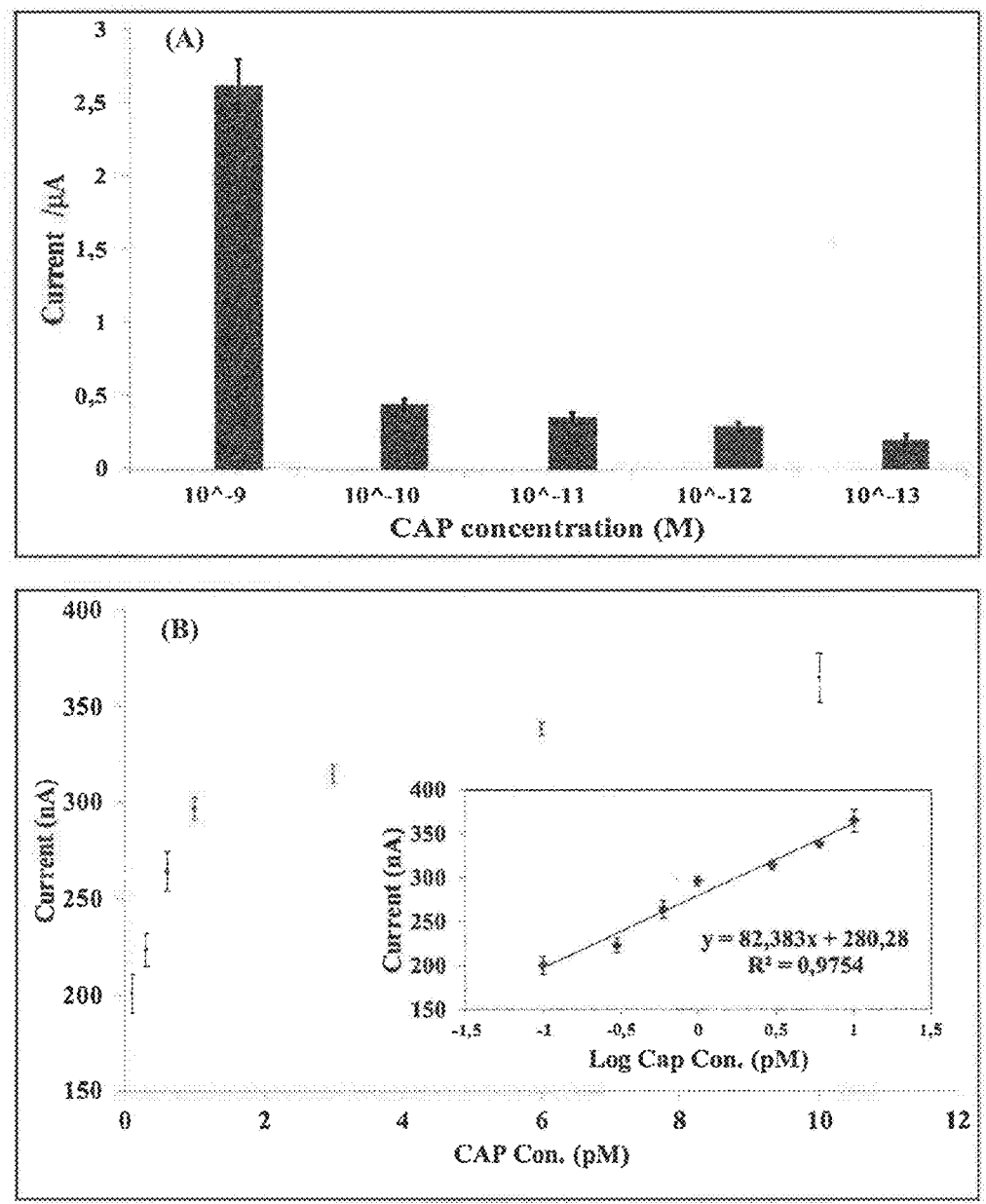

FIG. 17A and FIG. 17B show in (A) the dependence of the redox peak current on the concentration of CAP at a Gel B|APT|Au SPE electrode, and in (B) calibration curves obtained at APT|Au SPE (1) and Gel B|APT|Au SPE (2) electrodes.

ELECTRODE

The electrochemical aptasensor according to the present invention requires at least a detecting electrode, also named a working electrode. A conventional electrochemical device is a three-electrode cell configuration comprising a reference electrode (such as, but not limited to, a calomel electrode or a silver electrode) and a counter-electrode. Suitable detecting electrodes include gold electrodes, glassy carbon electrodes, an inert metal in an ionically conducting composite, and composite electrodes combining a polymeric material and electrically conducting particles. The electrode may be obtained by any manufacturing process known in the art, including the screen printing technique for making a SPE.

WO 2005/103664, the content of which is incorporated herein by reference, discloses suitable composite potentiometric electrodes for selective analyte detection-according to the present invention, provided that said electrodes are coated with an ionically conductive hydrophilic, preferably negatively charged, matrix such as gelatin type B or an equivalent thereof, for instance in the form of a thin (μm scale) or ultrathin (nm scale) layer. Gelatin B for performing this aspect of the invention may have any Bloom number, including the low range 50-125, the medium range 125-225 and the high range 225-325.

This composite electrode, and a potentiometric cell including it, may be for an in vivo analyte sensor or an in vitro analyte sensor.

Aptamer-Based Electrochemical Sensor

In a first aspect of the present invention, the above objective is realised by an aptamer-based electrochemical sensor, wherein said aptamer is covalently bonded to or chemisorbed on an electrode, said aptamer is selected to form a complex, usually a robust complex with a target molecule and is encapsulated by an ionically conductive hydrophilic, preferably negatively charged, matrix such as gelatin B or an equivalent thereof. Gelatin B for performing this aspect of the invention may have any Bloom number, including the low range 50-125, the medium range 125-225 and the high range 225-325.

According to a preferred embodiment of the first aspect of the present invention, said aptamer is selected with the SELEX procedure, or it may be known from the literature.

According to another preferred embodiment of the first aspect of the present invention, said target molecule is selected from the group consisting of vitamins, antibiotics, toxins, therapeutic drugs, diagnostic agents, recreational drugs (e.g. cocaine), catecholamines, metabolites, proteins and cells.

According to another preferred embodiment of the first aspect of the present invention, said aptamer is 5'-SH—(CH2)6-AGC-AGC-ACA-GAG-GTC-AGA-TGA-CTG-AGG-GCA-CGG-ACA-GGA-GGG-CAT-GGA-GAG-ATG-GCG-3' and is intended for CAP detection.

According to another preferred embodiment of the first aspect of the present invention, said aptamer is 5'-GTC-TCT-GTG-TGC-GCC-AGA-GAA-CAC-TGG-GGC-AGA-TAT-GGG-CCA-GCA-CAG-AAT-GAG-GCC-C-spacer-$NH_2$-3' and is intended for dopamine detection.

Method of Manufacturing an Electrochemical Sensor

In a second aspect of the present invention, the above objective is realised by a method of manufacturing an aptamer-based electrochemical sensor for determining a concentration of a target molecule comprising the steps of:
  selecting an aptamer to form a complex, preferably a robust complex, with a target molecule, e.g. using the SELEX procedure;
  synthesizing said aptamer;
  adsorbing said aptamer on or covalently coupling said aptamer with an electrode; and
  providing an ionically conductive hydrophilic, preferably negatively charged, matrix, preferably gelatin type B or an equivalent thereof, for said aptamer on said electrode.

According to a preferred embodiment of the second aspect of the present invention, said target molecule is selected from the group consisting of vitamins, antibiotics, toxins, therapeutic drugs, diagnostic agents, recreational drugs, catecholamines, metabolites, proteins and cells.

Use of the Aptamer-Based Electrochemical Sensor

In a third aspect of the present invention, the above objective is realised by the use of the aptamer-based electrochemical sensor according to the first aspect of the present invention or produced according to the second aspect of the present invention for the electrochemical determination of a concentration of a target molecule.

According to a preferred embodiment of the third aspect of the present invention, said electrochemical determination is a potentiometric determination.

According to another preferred embodiment of the third aspect of the present invention, said electrochemical determination is an amperometric determination.

EXAMPLES

Chemicals and Materials

Promazine, lidocaine, ritodrine and chloramphenicol (CAP) were obtained from Sigma-Aldrich (Bornem, Belgium) and dopamine (DA) was obtained from Fluka. To dissolve these drugs, small amounts of ethanol (Fluka, analytical grade) were used.

MES was obtained from Acros Organics (Eupen, Belgium).

The coupling agents EDC and NHS were obtained from Sigma-Aldrich.

All chemicals were of analytical reagent grade.

Type B gelatin (Gel, IEP=5, Bloom strength=257), isolated from bovine skin by the alkaline process, was provided by Tessenderlo Chemic (Belgium).

Buffers:
Tris buffer containing:

| | |
|---|---|
| NaCl | $100 \times 10^{-3}$ mol L$^{-1}$ |
| Tris HCl | $20 \times 10^{-3}$ mol L$^{-1}$ |
| MgCl$_2$ | $2 \times 10^{-3}$ mol L$^{-1}$ |
| KCl | $5 \times 10^{-3}$ mol L$^{-1}$ |
| CaCl$_2$ | $1 \times 10^{-3}$ mol L$^{-1}$ | with a pH of 7.6 obtained from VWR (Belgium) and used as a binding buffer solution.

Aptamers:

| | |
|---|---|
| binding aptamer sequence (5'-SH-(CH2)$_6$-AGC-AGC-ACA-GAG-GTC-AGA-TGA-CTG-AGG-GCA-CGG-ACA-GGA-GGG-CAT-GGA-GAG-ATG-GCG-3') | from Eurogentec. |
| A 58 mer aptamer selected specifically to detect DA (Zheng et al., 2011) (5'-GTC-TCT-GTG-TGC-GCC-AGA-GAA-CAC-TGG-GGC-AGA-TAT-GGG-CCA-GCA-CAG-AAT-GAG-GCC-C-spacer-NH$_2$-3') | aptamer synthesized by Integrated DNA Technologies (Leuven, Belgium) |

Voltammetric Measurements

Voltammetric measurements were recorded by μ-AutolabII potentiostat controlled by NOVA 1.7 software package (Metrohm, The Netherlands). Electrochemical impedance spectroscopy (EIS) measurements were performed by using a frequency response analyzer module. A gold electrode inlaid disk (Φ=1.6 mm) was used as working electrode. A saturated calomel electrode (SCE) and graphite were used as the reference and the auxiliary electrode, respectively.

Morphological Investigation

Morphological investigation of the electrode surface was performed using a JEOL JSM-6300 Scanning Electron Microscope (SEM) and confocal microscopy was performed by localizing Cy3 dyes with a Nikon C1 laser scanning confocal unit (D-eclipse-C1, Nikon, Melville, N.Y.) equipped with an argon and a helium/neon laser line fitted onto an upright microscope (Eclipse E600, Nikon, Melville, N.Y.) in combination with a 10× planfluor (NA: 0.50) objective manufactured by Nikon (Melville, N.Y.).

FIA

The FIA recordings were performed using a LC-10ADvp pump (Shimadzu Liquid Chromatography) and a Rheodyne 7125 six port external sample injector (VICI, US). A 1.00 mL sample loop was used to generate square concentration pulses for sensorgram recording in FIA conditions. The PEEK tubing (Alltech, USA) of the injection loop and the injector-detector connections had an internal diameter of 0.18 mm. The flow rate was 1.00 mL min$^{-1}$. Poiseuille peak broadening effects were kept to a minimum using short injector-detector connections (150 mm). To avoid such effects at the end of the square concentration pulse, the injector was switched from inject to load after 80 s (well before the sample loop volume was totally emptied).

This results in a sharp pulse with negligible broadening as well at the start as at the end of the pulse. The eluent was 10.0 mM MES. pH 7.0.

The column outlet was directed perpendicularly towards the sensitive membrane of the coated wire electrode in a "wall-jet" flow cell. The distance from the LC tubing outlet to the electrode was 0.10 mm.

Preparation of the Amperometric Electrode for Example 1

Prior to surface modification, the gold electrode was mechanically polished with 1.0 and 0.05 μm alumina slurry separately, followed by rinsing thoroughly with double distilled water. Then it was washed ultrasonically in double distilled water then ethanol for 15 minutes. The electrode was rinsed with distilled water and dried at room temperature. Subsequently, electrodes were electrochemically cleaned by potential scanning between −1.2 and 1.2 V until a reproducible cyclic voltammetric scan was obtained.

To immobilize the CAP-binding thiolated aptamer on the gold surface, $3 \times 10^{-6}$ L of a $2.5 \times 10^{-6}$ mol L$^{-1}$ aptamer and 5% (w/w) gelatin type B solution was dropped onto a freshly smoothed gold surface, and the solvent was then evaporated at 4° C. for 6 hours. The final sensing interface was ready after rinsing with buffer solution.

Preparation of the Potentiometric Electrode for Example 2

The indicator electrode is made of a PVC cylinder. It contains a cylindrical substrate electrode (3.0 mm diameter× 1.0 mm length), which is an electronically conducting graphite/PVC composite material. The composite substrate electrode was polished with Carbimet grid 600 (Buehler Ltd, USA).

To coat the gelatinous hydrogel on the electrode, 10.0 μL of a mixture, which consists of 25.0 mg gelatin B dissolved in 0.50 mL 10.0 mM MES (5% w/v) pH 7.0 at 40° C., was brought onto the electrode surface with a micropipette and exposed to air for 2 hours at 4° C. (drop drying).

The EDC-NHS coupling procedure was used to bind the DA-binding aminated aptamer covalently to the gelatin B hydrogel (which contains carboxyl groups). After adding 20 μL of the coupling agents (15.32 mg of EDC and 2.32 mg of NHS dissolved in 100 μl of 10.0 mM MES buffer at pH 7.0) to the coated hydrogel for 2 hours, 2×4 μL of the aptamer ($10^{-4}$M) was applied for 1 hour. After evaporation for 2 hours at 4° C. the electrodes were kept in 10.0 mM MES running buffer, pH 7.0 for at least 3 hours until a stable baseline was obtained. The sensorgrams of each analyte were measured on 3 electrodes, and used when the interelectrode reproducibility was better than 10%. At least 3 sensorgrams (injections) were recorded on each electrode after conditioning and stabilization in the running buffer.

The membrane potential was measured against an Orion 800500Ross® reference electrode (Ag/AgCl) using a high impedance ($10^{13}$Ω) homemade amplifier. The detection signals were recorded on a data station composed of a computer equipped with a 6013 NI DA converter and LabVIEW 7 (National Instruments, US) based software. The overall RC time constant of the high impedance amplifier plus data station was set to 0.2 s.

Example 1

Electrochemical CAP-aptasensor

Morphology

Figures 4A, 4B:
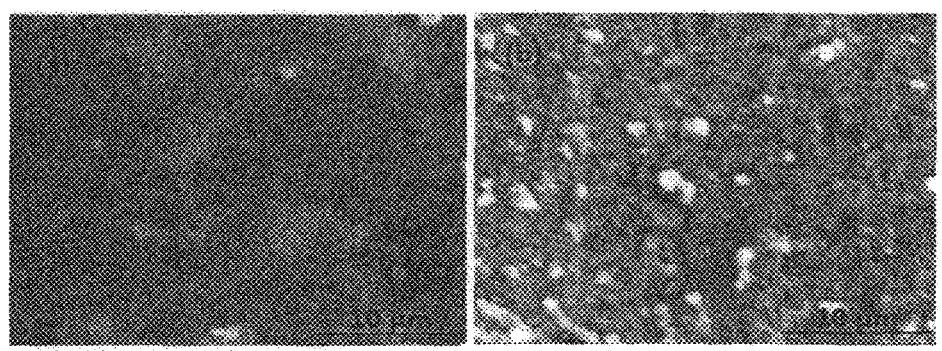
FIG. 4A and FIG. 4B show SEM images of the working surface area of a gold electrode after gelatin B immobilization (a), and after aptamer incorporation (b).

The morphology of the prepared electrodes was investigated by SEM measurements (see FIG. 4). The SEM image of a gelatin assembled gold electrode is shown in FIG. 4(a), a regular and porous structure being observed. The gelatin film was compact, smooth and homogenous without grainy and porous structure, showing that an ordered matrix was formed. However, a rough, sponge-like and irregular surface appeared when aptamers were added to the matrix, indicating a clear morphology change due to the interactions.

Figure 1:
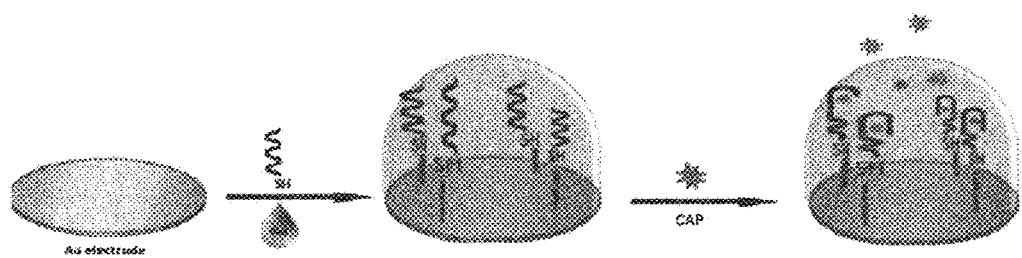
FIG. 1 is a representation of a gelatin-containing aptasensor for CAP detection on a gold (Au) electrode.
Figure 2:
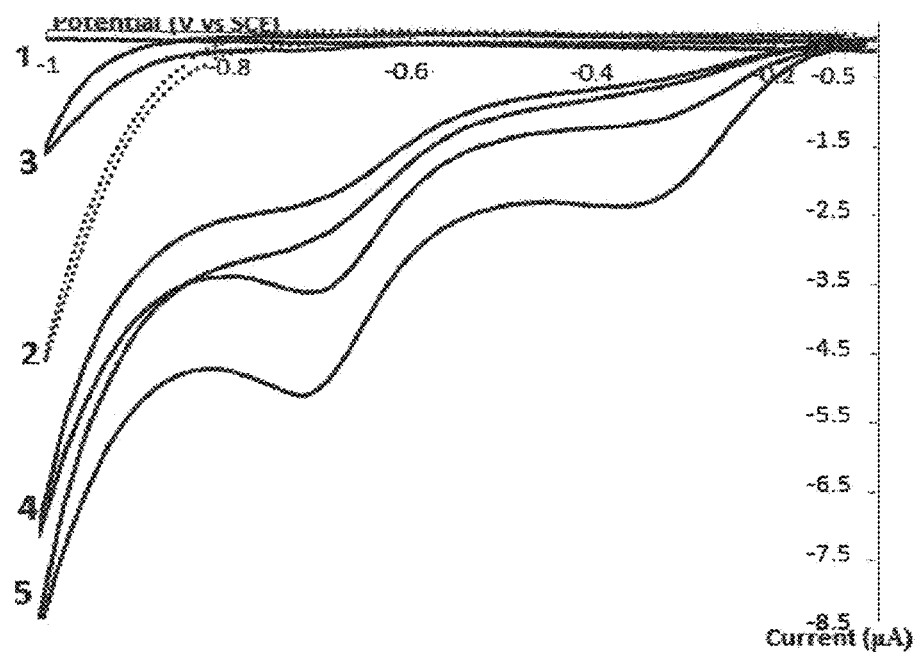
FIG. 2 shows cyclic voltammograms of Au (1), Gel B|APT|Au electrode (2) in blank solution and Au (3), APT|Au (4) and Gel B|APT|Au (5) electrode in $1 \times 10^{-6}$ mol $L^{-1}$ of CAP solution.
Figure 3:
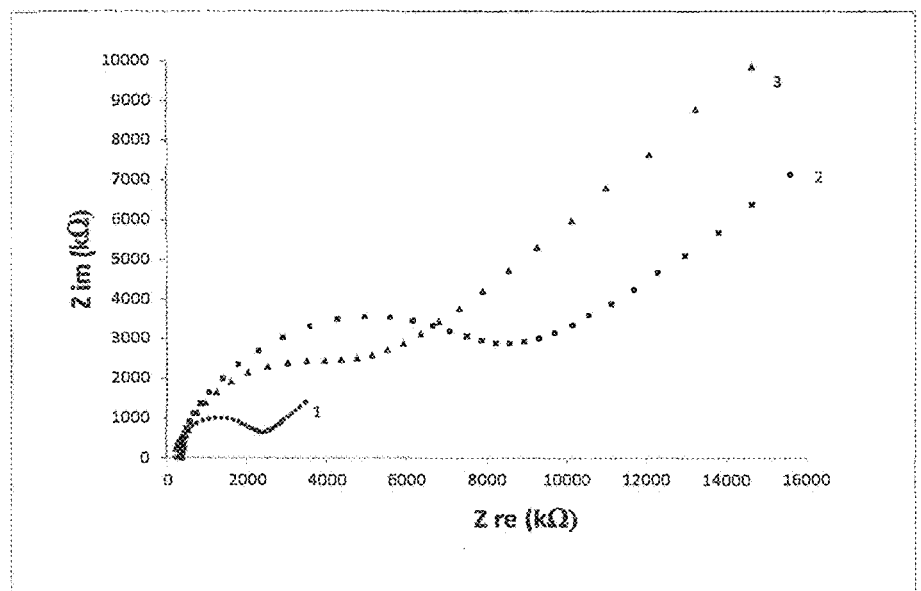
FIG. 3 shows the electrochemical impedance spectra of Au (1), APT|Au (2) and Gel B|APT|Au (3) electrode in $10 \times 10^{-3}$ mol $L^{-1}$ $[Fe(CN)_6]^{4-/3-}$ in the frequency range 0.1 to 100,000 Hz.

Electrochemical Behaviour:

Cyclic voltammetry (CV) and electrochemical impedance spectroscopy (EIS) measurements were performed to characterize an APT|Au electrode and a Gel B|APT|Au electrode as shown in FIGS. 2 and 3 respectively.

Whereas at a bare gold electrode no obvious redox peak was observed in the CV-characteristic (indicated by 3 in FIG. 2), a large reduction peak was observed in the CV-characteristic (indicated by 4 in FIG. 2) at APT|Au. With gelatin type B encapsulation the response (indicated by 5 in FIG. 2) increased due to the increased electron transfer capability of the modified electrode. A gelatin type B film acts as both a supporting polymer for aptamers and as a reaction medium. Therefore, substrate mass transport occurred in and out of the hydrogel layer while the aptamers were retained in the matrix and on the electrode surface.

The EIS characteristics shown in FIG. 3 demonstrate that the electron transfer resistance increased in the following order: Au electrode (indicated by 1 in FIG. 3), APT|Au electrode (indicated by 2 in FIG. 3) and Gel B|APT|Au electrode (indicated by 3 in FIG. 3). This is attributed to the fact that ssDNA with negative charges on its phosphate backbone makes an electrostatic repulsive force to the $[Fe-(CN)_6]^{3-/4-}$ anions and prevents electrons from reaching the electrode surface. The increase in electron transfer resistance indicates that the aptamers are successfully immobilized on the electrode surface. In the case of a Gel B|APT|Au electrode, an additional barrier of negatively charged gelatin has increased the electron transfer resistance which results in a larger semi-circle. This demonstrates the successful immobilization of APT on the electrode and the blocking effect of the gelatin layer to unspecific redox active molecules. The CV-characteristics of the resulting aptasensor at different scan rates were also studied. In the presence of CAP molecules, a linear dependence of peak current upon scan rate implied that the electrochemical process was a surface confined process. The short-term stability of the aptasensor was investigated over successive cyclic voltammograms. The response current of the electrode with immobilized aptamer and gelatin encapsulation decreased by about 3.2% of its initial response and the relative standard deviation (R.S.D.) was 1.8%, whereas the electrode only with immobilized aptamer showed a 20.2% decrease and an R.S.D. of 3.5%. The high stability could be attributed to the high chemical stability of gelatin and aptamers, both improving the stability of the aptasensor. The good stability of the Gel B|APT|Au can be ascribed to excellent biocompatibility and the stabilizing microenvironment around the aptamers provided by the modified gelatin sensors.

Figure 5A:
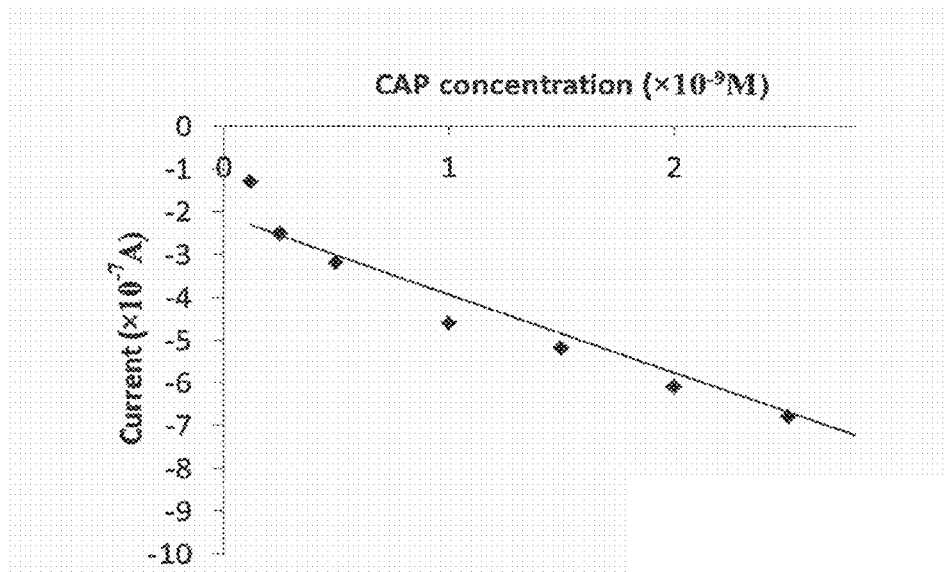
FIG. 5A and FIG. 5B show in (A) the dependence of the redox peak current on the concentration of CAP at a
Gel B|APT|Au electrode, and in (B) calibration curves obtained at APT|Au (1) and Gel B|APT|Au (2) electrodes.
Figure 5B:
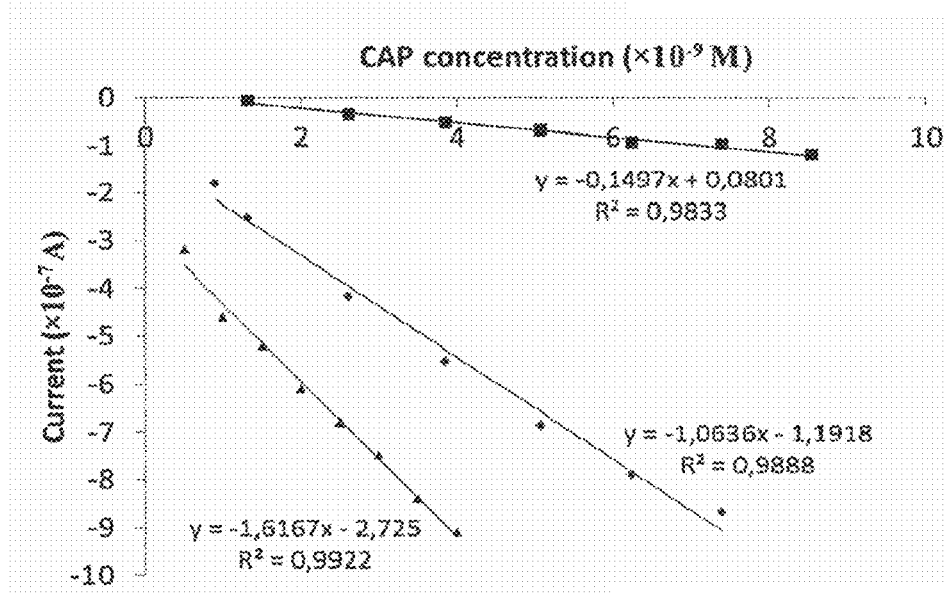

From FIG. 5(A), it can be seen that the peak current increases with increasing CAP concentration. There was a linear relationship between peak current and CAP concentration in the range from $2.1 \times 10^{-9}$ to $5.2 \times 10^{-7}$ mol L$^{-1}$. The linear regression equation was I=−1.6 C+2.7, (units for C and I are $\times 10^{-9}$ M and $\times 10^{-7}$ A respectively) and the correlation coefficient is 0.9684. The detection limit was $1.2 \times 10^{-9}$ mol L$^{-1}$ based on interpolation to the point where the current differs from the background current for three standard deviations calculated from the currents obtained for three different electrodes. In the case of APT|Au electrodes (without gelatin as a protective matrix), the detection limit was found to be $1.6 \times 10^{-9}$ and the linear range was between $1.6 \times 10^{-1}$ and $4.2 \times 10^{-7}$ mol L$^{-1}$ which demonstrated the improved performances of the Gel B|APT|Au electrode over the APT|Au electrode. The enhanced sensitivity and broader dynamic range could be due to the ability of gelatin B to make diffusion of analytes easier and prevent aptamers from leaking and most important, prevent the electrode surface from undesired adsorption. A comparison of the calibration curves for the two electrodes [see FIG. 5(B)] shows that the sensitivity (slope) of the Gel B|APT|Au electrode was higher than that of the APT|Au electrode.

The assay of this target in real samples was investigated by detecting CAP in a sample of skimmed cow's milk. The standard addition method was employed to evaluate the applicability of the developed aptasensor. The increased reduction peak of CAP compared with the reduction current obtained at an aptamer immobilized electrode without gelatin as protective matrix occurred at a Gel B|APT|Au electrode in the expected potential range, which indicated an enhanced sensitivity of the developed Gel B|APT|Au electrode. Recovery values between 87% and 94% were obtained, indicating the applicability of the developed aptasensor for CAP detection in real biological samples.

Example 2

Electrochemical DA-aptasensor

Morphology

Figure 6A:
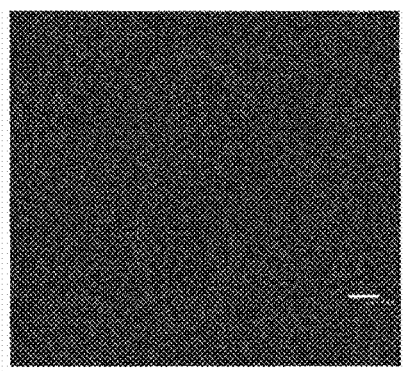
FIG. 6A, FIG. 6B, and FIG. 6C show in confocal images of hydrogels. (A): pure Gelatin B; (B):
Gelatin B+coupling agents (EDC and NHS); and (C): Gelatin B+coupling agents+fluorescent aptamer. Confocal features: pixels 7.92; red value 5.58; the scale bar (white)=100 μm.
Figure 6B:
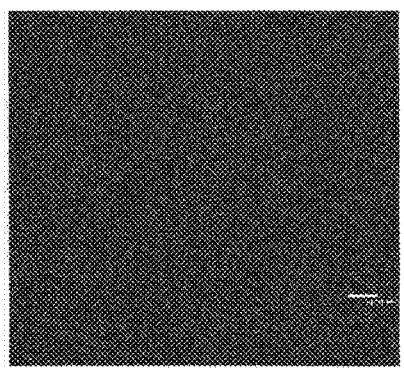
Figure 6C:
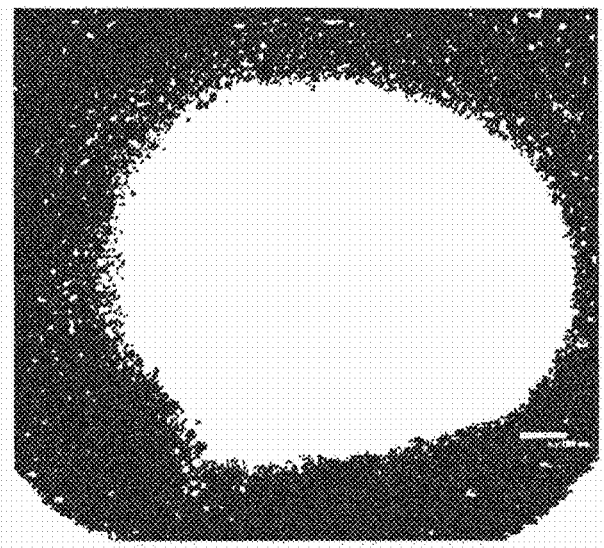

The covalent binding of the aminated oligonucleotides to the gelatin B, which contains carboxyl groups, was examined by confocal microscopy. To exclude the background signal, pure Gelatin B and Gelatin B treated with coupling agents (EDC and NHS), were checked as blanks. No signal was observed in the latter cases (FIGS. 6A and 6B). This is in contrast with the bright fluorescent signal observed for a hydrogel treated with a fluorescent labeled (Cy3) aminated aptamer (FIG. 6C). Even after three hours of use in the FIA potentiometric set-up, the intense fluorescence persisted. This experiment confirmed the covalent coupling of the aminated oligonucleotides to the gelatin B.

Electrochemical Behaviour

After checking the coupling of the aptamer to the biopolymer as described above, the electrodes were placed in a FIA potentiometric setup. After injection of an analyte in the FIA system, the voltage output varies with time, due to the kinetics of complex formation between DA and the anti-DA aptamer. A positively charged analyte molecule such as DA has the tendency to adsorb to the sensor coating, if a DA binding aptamer is present in this material. This provokes a surface potential change, which is our analytical signal. In its most simple representation, the eluent/gelatin B interface is expected to have a Boltzmann type distribution of positive charges as the gelatin B behaves as a cation exchange-like material in the given conditions.

Figure 7:
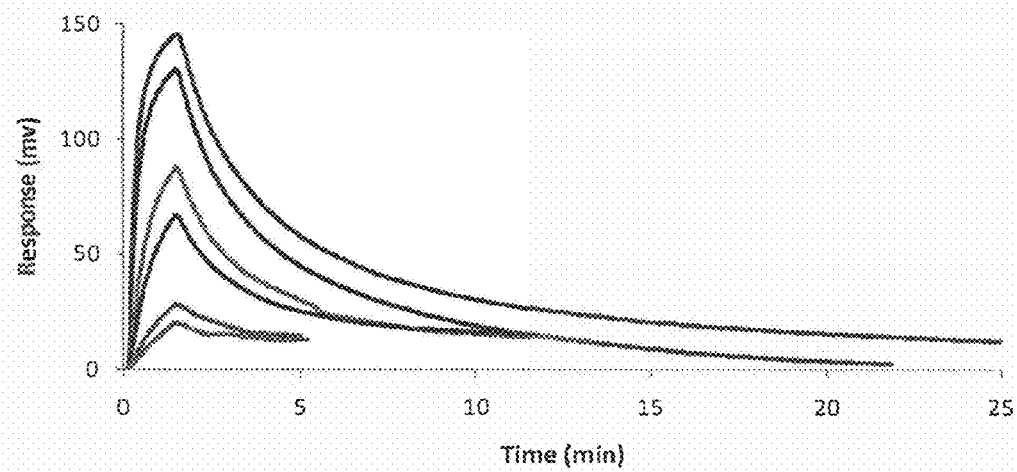
FIG. 7 shows sensorgram recordings for DA on a biosensor with a Gelatin B membrane with covalently linked aptamer. Square concentration pulses were injected for 80 s.
The concentration varied from $5 \times 10^{-7}$ M (lower curve) to $10^{-6}$ M, $5 \times 10^{-6}$ M, $10^{-5}$ M, $5 \times 10^{-5}$ M, and $10^{-4}$ M (upper curve).

The target molecules were injected as square concentration pulses, comparable with the block pulses in SPR. The sensorgrams (mV responses as a function of time) obtained are shown in FIG. 7. Using a hydrodynamic method and square concentration pulses has the advantage that both adsorption as desorption curves can be obtained and the adsorption/desorption kinetics calculated.

Figure 8:
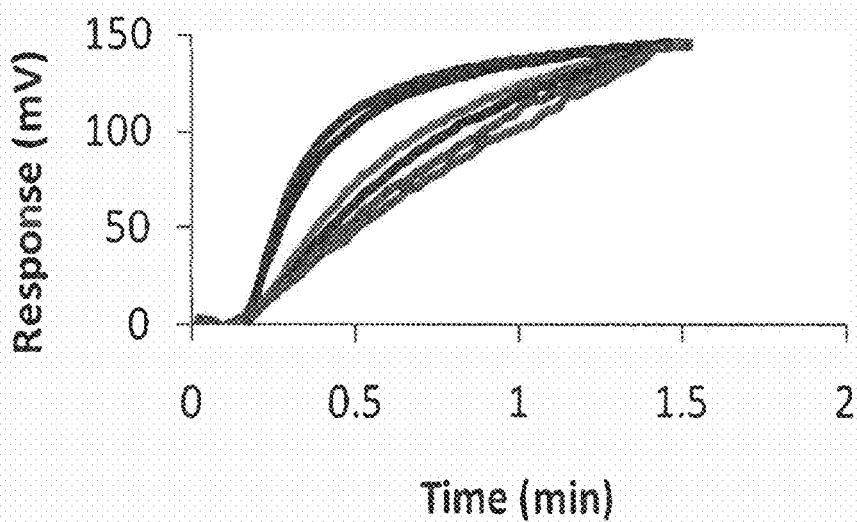
FIG. 8 shows normalisation of the curves in FIG. 7 from time 0 to the time corresponding to maximum response $R_{max}$ to a $10^{-4}$ M DA injection, to show the variation with concentration.

FIG. 7 shows the potentiometric response of DA on the sensor which contains the DA specific aptamer. The response heights (mV obtained at the plateau values after 80 s of injection) are concentration dependent: see FIGS. 7 and 9. After normalization of the curves from time zero to $R_{max}$ (see FIG. 8), it is clear that higher concentrations of DA show faster "on" kinetics than lower concentrations. This concentration dependent difference in adsorption kinetics (rising part of the curve) is typical for SPR experiments.

Figure 9:
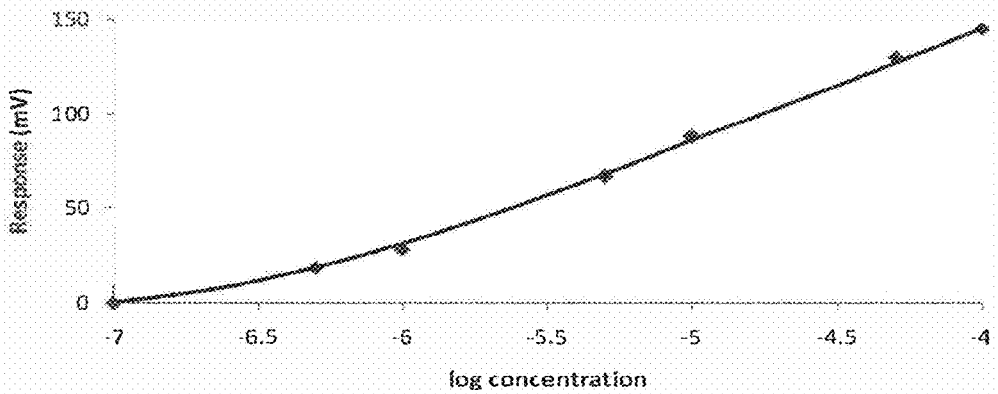
FIG. 9 shows a Nicolskii-Eisenmann-type calibration graph. The smooth curve is obtained from a non-linear least-squares fit to a Nicolskii-Eisenmann function of the type E=E°+S, log ($c_{DA}$+Cst). E°=387 mV, S=60.4 mV and Cst=$3.9 \times 10^{-7}$ M.

If the maximum responses (in mV) are plotted against the logarithm of the concentration, the typical Nicolskii-Eisenmann curve is obtained (see FIG. 9). At higher concentration values (results not shown), saturation of the signal (reaching a plateau value) starts to occur. This is ascribed to the fact that a relatively low aptamer concentration ($10^{-4}$ M) was used to bind to the hydrogel. DA concentrations below $5\times10^{-5}$ M were therefore used in these experiments.

The Nicolskii-Eisenmann equation (see FIG. 9) was transformed to equation 1, to obtain a concentration dependent output signal ("Transformed Response", tR) of the sensor.

$$tR = (10^{mV/S} - 1) \cdot Cst \qquad (1)$$

The transformed $R_{max}$ values (equation 1) of the potentiometric sensors with coupled aptamer were compared with the values obtained with electrodes which did not have an aptamer coupled to the hydrogel: see FIG. 9. Four electrodes were tested, each with 3 injections. From five to ten times higher signals were measured with the aptamer-containing electrodes. Not only the height, but also the shape of the sensorgram was different when comparing gelatin B membranes with and without coupled aptamer (see FIG. 9). The gelatin B electrodes containing aptamer always yielded slowly falling curves. This is additional evidence for the recognition by the aptamer of the target molecule. Slowly falling curves mean slow desorption kinetics. This yields small $k_{off}$ values, resulting in high $K_{association}$ values: see equation. 2.

$$K_{association} = \frac{k_{on}}{k_{off}} \qquad (2)$$

Figure 10:
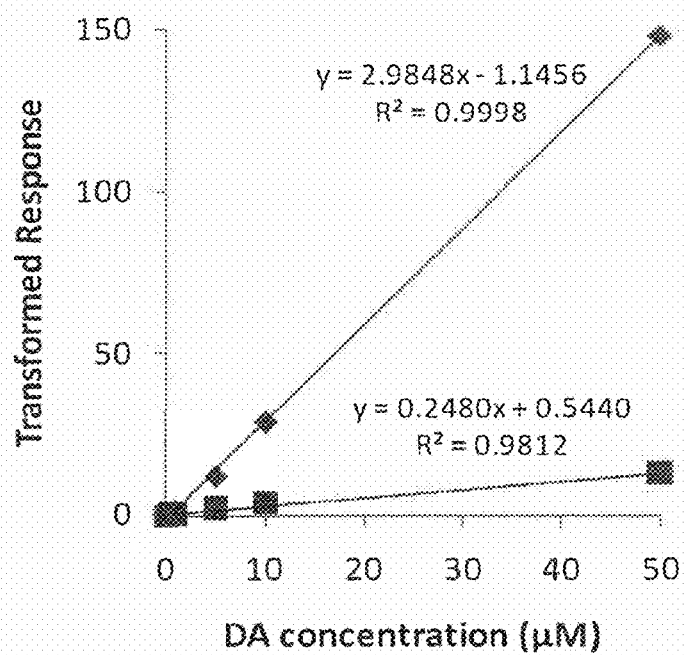
FIG. 10 shows the differences between the aptamer-based potentiometric biosensor (lighter upper trend line) and the negative control (darker lower trend line, only containing a Gelatin B membrane) in respect of the potentiometric responses of $5 \times 10^{-5}$M to $10^{-7}$ M DA injections in FIA after transformation to a concentration-related signal.
Figure 11:
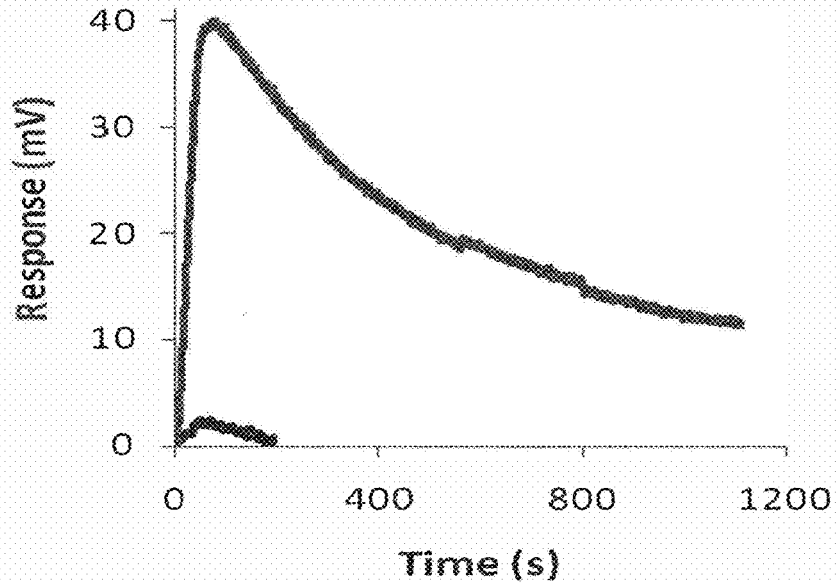
FIG. 11 shows the differences between the aptamer based potentiometric biosensor (lighter), and the negative control (darker) for injections of DA $10^{-6}$ M on a sensor which contains an aptamer (upper curve: lighter) and on a sensor which does not contain an aptamer (lower curve: darker).

FIGS. 9, 10 and 11 clearly show that the aptamer-based sensors are very sensitive, the responses being are at least a factor of 800 higher (on a mV basis) than those of the classical PVC-based electrodes.

Determination of the Association Constant, $K_{ass}$, Between DA-Specific Aptamer and DA The above-defined "sensorgram methodology" was used. Sensorgrams were recorded at different analyte concentrations. The rising parts of the sensorgrams are shown in mV in FIG. 8. The mV y-axis in these sensorgrams was first converted to a concentration dependent response, called transformed Response (see equation. 1). The transformed Response (tR) of the sensor was linearly related to the number of occupied adsorption sites, $R_{occupied}$, i.e.: transformed Response (tR)~$R_{occupied}$.

The rate of adsorption of DA, $v_{on}$, can be regarded as a reaction rate which is first order in the DA concentration in the bulk of the solution ($c_{analyte}$) and in the concentration of free adsorption sites (or aptamers) on the sensor surface: $R_{max} - R_{occupied}$. It can be described by a rate equation of the form of equation 3:

$$v_{on} = \frac{dR_{occupied}}{dt} = k_{on} \cdot c_{analyte}(R_{max} - R_{occupied}) - k_{off} R_{occupied} \qquad (3)$$

This equation can be rewritten by substituting the concentration of DA molecules, which adsorbed onto (or "occupied") the aptamer derivatized surface. $R_{occupied}$, by the sensor's transformed Response, tR, and by replacing $R_{max}$ by $tR_{max}$. This yields equation 4:

$$\frac{d(tR)}{dt} = k_{on} \cdot c_{analyte} \cdot d(tR)_{max} - (k_{on} \cdot c_{analyte} + k_{off}) \cdot tR \qquad (4)$$

Figure 12:
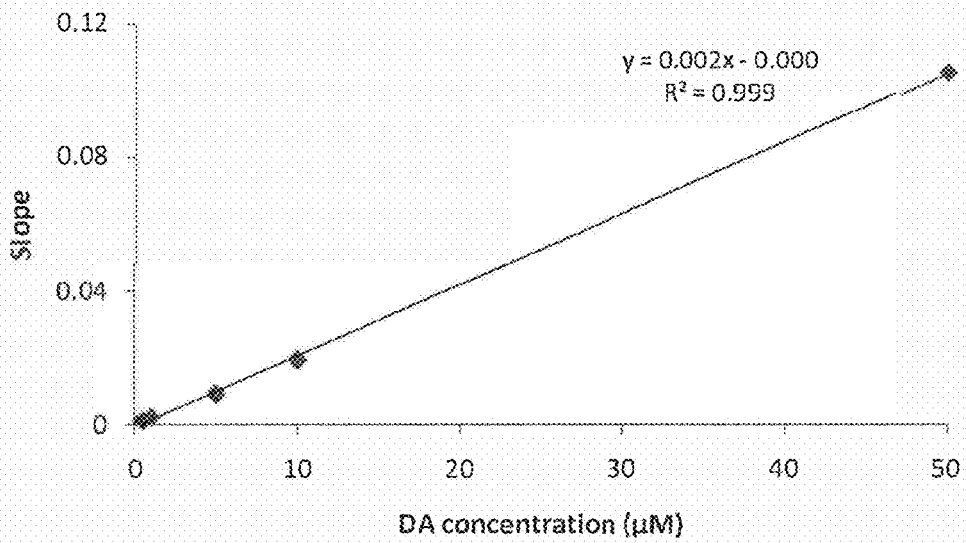
FIG. 12 shows the slope of $$\frac{d(tR)}{dt}$$

The first derivative of the rising up-going part of the transformed Response (tR) with time $$\frac{d(tR)}{dt},$$

was plotted against the transformed Response, tR. This yielded a straight line with a slope equal to $-(k_{on} \cdot c_{analyte} + k_{off})$. Plotting this slope versus $c_{analyte}$ for the set of analyte concentrations (DA) yielded a graph from which $k_{on}$ and $k_{off}$ were calculated. The "Slope" versus DA concentration curve obtained is given in FIG. 12, which confirms that the model used for the sensorgram methodology is applicable. For the first time reliable molecular interaction data were obtained for the interaction of a biomolecule (the aptamer) with its target molecule, via a potentiometric sensor principle.

Specific Detection with DA-Specific Aptamer

To check the specificity of the DA-specific aptamer, Dopamine and three other basic drugs (ritodrine, lidocaine and promazine) were tested on the gelatin B-coated electrodes with and without the aptamer. These lipophilic cationic drugs have much better responses on PVC-based potentiometric sensors than DA. Sensors based on gelatin B were quite insensitive towards these three other drugs, there being no improvement in sensitivity for these compounds when the aptamer biorecognition element was coupled to the gelatin B, whereas DA showed a very clear increase in $R_{max}$, as disclosed above. Table 1 gives the $R_{max}$ values (in mV) of $10^{-5}$ M injections of different analyte molecules for different potentiometric electrodes.

TABLE 1

| Coating | Dopamine response in mV | Ritodrine response in mV | Lidocaine response in mV | Promazine response in mV |
|---|---|---|---|---|
| Gelatin B | 9.46 | 1.83 | 2.88 | 3.66 |
| Gelatin B + DA-specific aptamer | 92.86 | 1.57 | 1.57 | 2.44 |

Example 3

Electrochemical CAP-aptasensor Based on a SPE Gold Electrode

Electrochemical measurements were recorded by a Autolab potentiostat controlled by NOVA 1.10 software package (Metrohm, The Netherlands). Morphological investigation of the electrode surface was done on a Fei Quanta 250 FEG Scanning Electron Microscope (SEMI). The SPE was purchased from Metrohm and made of a gold working electrode, a carbon counter electrode and a silver reference electrode.

Unless specified otherwise, the chemicals and materials are the same as in the previous examples.

FIG. 13 schematically shows the construction of the electrochemical gelatin type B-based CAP-aptasensor. In the absence of CAP, the thiolated aptamer encapsulated in gelatin B is partially un-folded but linked to the gold surface by an Au—S bonding. When CAP is introduced to the modified SPE, the aptamer switches its structure to bind CAP bringing the redox active molecules proximate to the electrode surface resulting in an enhanced electron transfer.

The first step is the electrochemical pre-treatment and biomodification of the gold screen printed electrode (SPE). Prior to immobilization of the thiolated DNA aptamer, a multiple-pulse amperometric pre-treatment of the gold surface is carried out in a stirred 0.5 mol L$^{-1}$ H$_2$SO$_4$, 10 mmol L$^{-1}$ KCl solution. The following triple-potential pulse sequence: −0.3 V for 3.0 s; 0.0 V for 3.0 s and +1.0 V for 1.5 s (15 cycles) was applied. The gold working electrode surface of SPE was then exposed to the mixture of aptamer (5 µM) and the solution of gelatin type B (5 w/v %) in tris buffer (pH 7.6). The percentage of the incorporation was 70:30 v/v % from the aptamer:gel mixture. Chemisorption is allowed to proceed (about 4 hours) while the electrodes are stored in a wet chamber to protect the solution from evaporation. The immobilization step is followed by addition of CAP solution (a 100 µL drop) on top of the modified-gold SPE for 25 minutes. Prior to the electrochemical measurement, the electrode was gently washed with 100 µL of tris buffer. Then, the differential pulse voltammetry is performed in tris buffer solution (pH 7.6).

EIS measured data (FIG. 14) show that the electron transfer resistance increases in the following order: bare SPE (FIG. 14a), aptamer modified SPE (FIG. 14b) and aptamer/Gelatin B modified SPE (FIG. 14c). The increase in electron transfer resistance indicates that the aptamers are successfully immobilized on the electrode surface. In the case of a aptamer/GelB SPE, an additional barrier of negatively charged gelatin has increased the electron transfer resistance which results in a larger semi-circle. This demonstrates the successful immobilization of the aptamer on the SPE electrode and the blocking effect of the gelatin B layer against unspecific redox active molecules.

In order to investigate the role of the gelatin B matrix in the efficiency of the aptasensor, differential pulse voltammetry (DPV) was selected as sensitive technique. FIG. 15 displays the differential pulse voltammograms of accumulated CAP (10$^{-9}$ M) at the surface of bare gold SPE (curve a: 0.00 µA), Gelatin A modified SPE (curve b: 0.67 µA±0.02), Gelatin B modified SPE (curve c: 0.801±0.015 µA), aptamer modified SPE (curve d: 1.22±0.06 µA), aptamer/Gelatin A modified SPE (curve e: 0.86±0.04 µA) and aptamer/Gelatin B modified SPE (curve f: 2.71±0.09 µA) in tris buffer solution. The indicated currents reflect the peak current obtained in the voltammogram and can be explained as the irreversible reduction of the nitro group (NO$_2$) present in CAP molecules, with formation of hydroxylamine (NHOH). As can be seen, there is no signal for CAP at a bare gold electrode. It means that no chemisorption takes place after 25 minutes accumulation of CAP at the surface of bare gold SPE (curve a). After immobilization of gel at SPE, the DPV signal appears for accumulated CAP (curve b and c). However, Gelatin B modified SPE shows a higher current signal than Gelatin A. Following the modification of the SPE by the aptamer, the current of DPV signal increased (curve d), confirming the ability of the synthesized aptamer to capture the target molecule. The combination of aptamer and Gelatin A had no positive effect on the sensor efficiency (curve e) while the incorporation of aptamer and Gelatin B showed a very good response toward the target molecule (curve f) at the potential at which we expect the reduction of the nitro group, i.e. −0.7 V. Also, there is a pre oxidation wave around −0.45V that shows the presence of intermediates in redox reactions of CAP.

Dramatic increase in DPV height after mixing aptamer and Gelatin B is likely due to an increase in charge transfer kinetics resulting from the better reactivity of the aptamer towards the target. Due to the incorporation of the aptamer in the gelatin B matrix and its biocompatibility, most sites of the aptamer will remain active during the formation of the self-assembled monolayer from the thiolated aptamer. As the mixture of aptamer/gelatin B shows a significantly higher DPV signal than aptamer/gelatin A, the biocompatibility of gelatin B towards aptamers is expected to be better. Because of the physical interactions between the aptamer chains and gelatin (e.g. van der Waals forces and hydrogen bonds between amino acids), GelB is a good example of a physically cross-linked hydrogel. Therefore, the hydrophilic groups or domains which are hydrated make GelB a suitable matrix for the entrapment of the aptamer.

To obtain the most sensitive results, parameters such as the kind (FIG. 16A) and time (FIG. 16B) of the CAP accumulation step were optimized for the electrochemical detection of CAP. Three approaches were investigated to accumulate CAP on the surface of the aptamer/GelB electrodes. First, the modified SPE was immersed in the CAP solution while the solution was stirred very fast (i). Secondly, the CAP solution was stirred slowly (ii). Thirdly the modified SPE was kept horizontally with a 100 µL of the CAP solution on top of it (wet drop, iii). The latter was proven to be the best to accumulate CAP because of the better interaction opportunity between CAP, aptamer, GelB and the electrode surface (FIG. 16A). Also, the time of accumulation for CAP on the surface of the aptamer/GelB modified SPE was investigated during 10, 15, 20, 25, 30 and 35 minutes. When accumulation time increased from 10 to 25 minutes, the signal of the accumulated CAP enhanced. After that, no obvious changes in the DPV reduction current of CAP were observed. Therefore, 25 minutes was selected as optimized time (FIG. 16B).

FIG. 17A depicts the diagnostic performance of the aptasensor. To study the role of gelatin B as matrix in function of the biosensor, the CAP reduction signal was investigated on the aptamer/gelatin B modified SPE. It can be seen that the peak current increases with an increase of the concentration of CAP (FIG. 17B). The peak current shows a linear relationship with the Log of concentration of CAP in the range from 0.10 to 10.0 pico mol L$^{-1}$ (insert of FIG. 17B). The calculated detection limit is 2.09×10$^{-14}$ mol L$^{-1}$ based on the interpolation to the point where the current differs from the background current for three standard deviations calculated from the currents obtained for three different electrodes.

Example 4

Selective CAP Detection in a Milk Sample

The assay of the target in a real sample was investigated by detecting CAP in a skimmed cow's milk sample with the SPE electrode of example 3. The standard addition method was employed to evaluate the applicability of the developed aptasensor. The increased reduction peak of CAP occurred in the expected potential range at aptamer/gelatin B modified SPE compared to the reduction current obtained at an aptamer immobilized electrode without a gelatin protective matrix, suggesting an enhanced sensitivity of the developed sensor. Recovery values shown in table 2, ranging between 82% and 95%, indicate the applicability of the developed aptasensor for CAP detection in real samples.

TABLE 2

| Sample | Added (M) | Detected (M) | Recovery (%) | R.S.D. (%) |
|---|---|---|---|---|
| 1 | $10^{-9}$ | $9.50 \pm (0.36) \times 10^{-10}$ | 95 | 3.78 |
| 2 | $10^{-10}$ | $8.60 \pm (0.30) \times 10^{-11}$ | 86 | 3.48 |
| 3 | $10^{-11}$ | $8.23 \pm (0.26) \times 10^{-12}$ | 82 | 3.15 |

For selectivity study, thiamphenicol and florfenicol antibiotics with a structure similar to CAP were used. Results showed that they did not influence the performance of the aptasensor, suggesting a good selectivity of this aptasensor. Also for stability study, the impedance measurement was done after a CAP electrochemical detection. The same value was obtained, indicating that the self-assembled aptamer is quite stable.

The invention claimed is:

1. A composite electrode combining a polymeric material and electrically conducting particles, wherein said electrode is coated with a type B gelatin.

2. A composite electrode according to claim 1, wherein the polymeric material is plasticized polyvinyl chloride.

3. A composite electrode according to claim 1, wherein the electrically conducting particles are graphite powder.

4. A composite electrode according to claim 1, wherein the polymeric material is plasticized polyvinyl chloride and wherein the electrically conducting particles are graphite powder.

5. A composite electrode according to claim 1, wherein an aptamer is covalently bonded to, or chemisorbed on, said electrode.

6. A composite electrode according to claim 1, wherein an aptamer is covalently bonded to, or chemisorbed on, said electrode, wherein the aptamer is selected to form a robust complex with a target molecule, and wherein the target molecule is selected from the group consisting of vitamins, toxins, antibiotics, therapeutic drugs, diagnostic agents, recreational drugs, catecholamines, metabolites, proteins, and cells.

7. A composite electrode according to claim 1, wherein an aptamer is covalently bonded to, or chemisorbed on, said electrode, wherein the aptamer is selected to form a robust complex with a target molecule, and wherein the target molecule is dopamine and the aptamer is GTC-TCT-GTG-TGC-GCC-AGA-GAA-CAC-TGG-GGC-AGA-TAT-GGG-CCA-GCA-CAG-AAT-GAG-GCC-C (SEQ ID NO:3).

8. A composite electrode according to claim 1, wherein an aptamer is covalently bonded to, or chemisorbed on, said electrode, wherein the aptamer is selected to form a robust complex with a target molecule, and wherein the target molecule is chloramphenicol and the aptamer is AGC-AGC-ACA-GAG-GTC-AGA-TGA-CTG-AGG-GCA-CGG-ACA-GGA-GGG-CAT-GGA-GAG-ATG-GCG (SEQ ID NO:1) or the aptamer is AGC-AGC-ACA-GAG-GTC-AGA-TGA-CTG-AGG-GCA-CGG-ACA-GGA-GGG-GGA-GAG-ATG-GCG-TGA-GGT-CCT-ATG-CGT-GCT-ACC-GTG-AA (SEQ ID NO:2).

9. A composite electrode according to claim 1, wherein an aptamer is covalently bonded to, or chemisorbed on, said electrode, wherein the aptamer is selected to form a robust complex with a target molecule, and wherein the target molecule is cocaine or heroin.

10. A composite electrode according to claim 3, wherein an aptamer is covalently bonded to, or chemisorbed on, said electrode.

11. A composite electrode according to claim 3, wherein an aptamer is covalently bonded to, or chemisorbed on, said electrode, wherein the aptamer is selected to form a robust complex with a target molecule, and wherein the target molecule is selected from the group consisting of vitamins, toxins, antibiotics, therapeutic drugs, diagnostic agents, recreational drugs, catecholamines, metabolites, proteins and cells.

* * * * *

```
                     SEQUENCE LISTING

<160> NUMBER OF SEQ ID NOS: 5

<210> SEQ ID NO 1
<211> LENGTH: 57
<212> TYPE: DNA
<213> ORGANISM: Artificial Sequence
<220> FEATURE:
<223> OTHER INFORMATION: Aptamer

<400> SEQUENCE: 1
agcagcacag aggtcagatg actgagggca cggacaggag ggcatggaga gatggcg        57

<210> SEQ ID NO 2
<211> LENGTH: 80
<212> TYPE: DNA
<213> ORGANISM: Artificial Sequence
<220> FEATURE:
<223> OTHER INFORMATION: Aptamer

<400> SEQUENCE: 2
agcagcacag aggtcagatg actgagggca cggacaggag ggggagagat ggcgtgaggt     60
cctatgcgtg ctaccgtgaa                                                  80

<210> SEQ ID NO 3
<211> LENGTH: 58
<212> TYPE: DNA
<213> ORGANISM: Artificial Sequence
<220> FEATURE:
<223> OTHER INFORMATION: Aptamer

<400> SEQUENCE: 3
gtctctgtgt gcgccagaga acactggggc agatatgggc cagcacagaa tgaggccc       58

<210> SEQ ID NO 4
<211> LENGTH: 57
<212> TYPE: DNA
<213> ORGANISM: Artificial Sequence
<220> FEATURE:
<223> OTHER INFORMATION: Aptamer. The 5' extremity carries a group
      -SH-(CH2)6-

<400> SEQUENCE: 4
agcagcacag aggtcagatg actgagggca cggacaggag ggcatggaga gatggcg        57

<210> SEQ ID NO 5
<211> LENGTH: 57
<212> TYPE: DNA
<213> ORGANISM: Artificial Sequence
<220> FEATURE:
<223> OTHER INFORMATION: Aptamer. The 3' extremity carries a group
      -C-spacer-NH2

<400> SEQUENCE: 5
gtctctgtgt gcgccagaga acactggggc agatatgggc cagcacagaa tgaggcc        57
```